United States Patent [19]

Shayman et al.

[11] Patent Number: 5,302,609

[45] Date of Patent: Apr. 12, 1994

[54] TREATMENT OF DIABETIC NEPHROPATHY

[75] Inventors: James A. Shayman; Norman S. Radin, both of Ann Arbor, Mich.

[73] Assignee: The Regents of the University of Michigan, Ann Arbor, Mich.

[21] Appl. No.: 991,574

[22] Filed: Dec. 16, 1992

[51] Int. Cl.$^5$ .................. A61K 31/42; A61K 31/195; A61K 31/16
[52] U.S. Cl. .................................. 514/380; 514/561; 514/625; 514/629; 514/866
[58] Field of Search .................... 514/237.8, 380, 561, 514/625, 629, 866

[56] References Cited

U.S. PATENT DOCUMENTS

| | | | |
|---|---|---|---|
| 3,573,925 | 4/1971 | Harned | 514/380 |
| 5,041,441 | 8/1991 | Radin et al. | 514/237.8 |
| 5,061,721 | 10/1991 | Cordi et al. | 514/561 |

FOREIGN PATENT DOCUMENTS

49-35975  9/1974  Japan .

OTHER PUBLICATIONS

Shukla, G. S. et al., "Rapid Kidney Changes Resulting from Glycosphingolipid Depletion by Treatment with a Glucosyltransferase Inhibitor", *Bioch. Biophys. Acta*, 1083:101–108 (1991).

Brownlee, M., "Glycosylation Products as Toxic Mediators of Diabetic Complications", *Annu. Rev. Med.*, 42:159–166 (1991).

Holleran, W. M. et al., "Sphingolipids Are Required for Mammalian Epidermal Barrier Function", *J. Clin. Invest.*, 88:1338–1345 (1991).

Shukla, A. et al., "Metabolism of D-[$^3$H]threo-1-phenyl-2-decanoylamino-3-morpholino-1-propanol, An Inhibitor of Glucosylceramide Synthesis, and the Synergistic Action of an Inhibitor of Microsomal Monooxygenase", *J. Lipid Res.*, 32:713–722 (1991).

Shayman, J. A. et al., "Glucosphingolipid Dependence of Hormone-stimulated Inositol Trisphosphate Formation", *J. Biol. Chem.*, 265:12135–12138 (1990).

Craven, P. A. et al., "Increase in Diacylglycerol Mass in Isolated Glomeruli by Glucose from De Novo Synthesis of Glycerolipids", *Diabetes*, 39:667–674 (1990).

Shukla, G. S. et al., "Glucosylceramide Synthase of Mouse Kidney: Further Characterization with an Improved Assay Method", *Arch. Biochem. Biophys.*, 283:372–378 (1990).

Medlock, K. A. et al., "Inhibition of Serine Palmitoyltransferase in Vitro and Long-Chain Base Biosynthesis in Intact Chinese Hamster Ovary Cells by β-Chloroalanine", *Biochem.*, 27:7079–7084 (1988).

Radin, N. S. et al., "Glucosphingolipids as Sites of Action in the Chemotherapy of Cancer", *Biochem. Pharmacol.*, 37:2879–2886 (1988).

Inokuchi, J. et al., "Preparation of the Active Isomer of 1-phenyl-2-decanoylamino-3-morpholino-1-propanol, Inhibitor of Murine Glucocerebroside Synthetase", *J. Lipid Res.*, 28:565–571 (1987).

Coste, H. et al., "Topology of Glucosylceramide Synthesis in Golgi Membranes from Porcine Submaxillary Glands", *Biochem. Biophys. Acta*, 858:6–12 (1986).

Beyer-Mears, A. et al., "Glomerular Polyol Accumulation in Diabetes and its Prevention by Oral Sorbinil", *Diabetes*, 33:604–607 (1984).

Spiro, M. J., "Effect of Diabetes on the Sugar Nucleotides in Several Tissues of the Rat", *Diabetologia*, 26:70–75 (1984).

Touchstone, J. C. et al., "(3-sn-Phosphatidyl)cholines (Lecithins) in Amniotic Fluid", *Clin. Chem.*, 29:1951–1954 (1983).

(List continued on next page.)

*Primary Examiner*—Frederick E. Waddell
*Assistant Examiner*—Raymond J. Henley, III
*Attorney, Agent, or Firm*—Harness, Dickey & Pierce

[57] ABSTRACT

The present invention is a novel method for the treatment of renal hypertrophy and hyperplasia associated with diabetic nephropathy. The method of the present invention generally comprises the administration to the diabetic patient of a compound which inhibits glycosphingolipid synthesis, more particularly, an inhibitor of GlcCer synthase or 3-ketodihydrosphingosine synthase.

16 Claims, No Drawings

OTHER PUBLICATIONS

Weinberg, J. M. et al., "Alterations in Renal Cortex Cation Homeostasis During Mercuric Chloride and Gentamicin Nephrotoxicity", *Exp. Mol. Pathol.*, 39:43-60 (1983).

Cortes, P. et al., "Effects of Early Diabetes on Uridine Diphosphosugar Synthesis in the Rat Renal Cortex", *Kidney Int.*, 21:676-682 (1982).

Weibel, "Stereological Methods. Practical Methods for Biological Morphometry", (Academic Press, London) pp. 44-45 (1979) (article not provided) as applied by Hirose, K. et al., Development of Glomerular Lesions in Experimental Long-Term Diabetes in the Rat, *Kidney Int.*, 21:689-695 (1982).

Radin, N. S., "Preparative Isolation of Cerebrosides (Galactosyl and Glucosyl Ceramide)", *J. Lipid Res.*, 17:290-293 (1976).

Keppler, D. et al., "Enzymic Determination of Uracil Nucleotides in Tissues", *Anal. Biochem.*, 38:105-114 (1970).

Shayman, J. A. et al., "Is Diabetic Nephropathy An Acquired Sphingolipidosis?", *J. of Cell. Biochem.*, p. 159 (1992).

Zador, I. Z. et al., "The Role of Glycosphingolipids in the Development of Diabetic Nephropathy", *Diabetes* (1992).

Futerman, A. H. et al., "Determination of the Intracellular Sites and Topology of Glucosylceramide Synthesis in Rat Liver", *Biochem. J.*, 280:295-302 (1991).

Dinur, T. et al., "Synthesis of a Fluorescent Derivative of Glucosyl Ceramide for the Sensitive Determination of Glucocerebrosidase Activity", *Anal. Biochem.*, 136:223-234 (1984).

Radin, N. S. et al., "Metabolic Effects of Inhibiting Glucosylceramide Synthesis With PDMP and Other Substances", *Advances in Lipid Res.* (1993) (in press).

Zador, I. Z. et al., "A Role for Glycosphingolipid Accumulation in the Renal Hypertrophy of Streptozotocin-induced Diabetes Mellitus", *J. Clin. Invest.*, 91:1-7 (1993).

Abe, A. et al., "Improved Inhibitors of Glucosylceramide Synthase", *J. Biochem.*, 111:191-196 (1992).

Mahdiyoun, S. et al., "Decreased Formation of Inositol Trisphosphate in Madin-Darby Canine Kidney Cells Under Conditions of $\beta$-Glucosidase Inhibition", *Arch. Biochem. Biophys.*, 292:506-511 (1992).

Shukla, A. et al., "Control of Kidney Size by Sex Hormones: Possible Involvement of Glucosylceramide", *Amer. Physiol. Soc.*, F24-F29 (1992).

Shayman, J. A. et al., "Modulation of Renal Epithelial Cell Growth by Glucosylceramide", *J. Biolog. Chem.*, 266:22968-22974 (1991).

Shayman, J. A. et al., "Structure and Function of Renal Glycosphingolipids", *Amer. Physiol. Soc.*, F291-F302 (1991).

TREATMENT OF DIABETIC NEPHROPATHY

SPONSORSHIP

This invention was made with government support under Grant No. DK 41487 awarded by the National Institutes of Health. The government has certain rights in the invention.

FIELD OF THE INVENTION

The present invention provides a novel method for the treatment of diabetic nephropathy, more particularly, the treatment of renal hypertrophy and hyperplasia by administering compounds which inhibit glycosphingolipid synthesis.

BACKGROUND OF THE INVENTION

Diabetes is a major cause of morbidity and mortality in the United States, with approximately 40 percent of all diabetic patients developing nephropathy which requires either kidney dialysis or transplantation. Specifically, diabetes mellitus is the leading cause of end stage renal disease and therefore, any newly diagnosed patient with diabetes mellitus would be considered at risk for the development of diabetic nephropathy. Several years prior to the development of renal insufficiency, diabetic patients also exhibit renal disease manifested by renal hypertrophy and hyperfiltration. Currently the only treatment suggested to prevent or reverse the renal hypertrophy of diabetic nephropathy is rigorous insulin therapy, although in practical application, insulin therapy has yielded disappointing results.

Under conditions of hyperglycemia, several normally minor pathways of glucose metabolism become more prominent. In the kidney these include the formation of sorbitol, the non-enzymatic glycosylation of proteins, and the de novo formation of diradyl glycerides. Beyer-Mears, A. L. et al., *Diabetes* 33:604–607 (1984); Brownlee, M., *Annual Rev. Med.* 42:159–166 1991); Craven, P. A. et al., *Diabetes* 39:667–674 (1990). These pathways are the basis for recent hypotheses on the mechanisms of diabetic complications, including nephropathy. In addition, increases in uridinediphospho-hexose (UPD-hexose) levels have been reported in the kidney and other organs in association with experimental diabetes. Cortes, P. et al., *Kidney Int.* 21:676–682 (1982); Spiro, M. J. *Diabetologia* 26:70–75 (1984). In particular, levels of uridinediphospho-glucose (UDP-Glc) were demonstrated to be consistently increased in early diabetes. This change has been postulated to increase the expression of glycoproteins and glycosaminoglycans in the basement membranes of diabetic tissues. Glycosphingolipids (GSLs), however, also require nucleotide-hexoses for their synthesis.

Glycosphingolipids are ubiquitous and complex molecules consisting of a lipid and a carbohydrate moiety. Glycosphingolipids are at the basis of several inherited metabolic disorders, and are also functionally important in organ development, growth, hormonal signalling and infection. Studies on the functional role of sphingolipids in the kidney and related tissue have focused mainly on their role in modulating growth through effects on phospholipase C and protein kinase C (PKC) activities. In particular, glucosylceramide (GlcCer) and related glycosphingolipids have been implicated in both the growth of cells and in the regulation of hormonal signaling.

In one study using Madin-Darby canine kidney (MDCK) cells, endogenous glycosphingolipid content was decreased by the glucosylceramide synthase inhibitor 1-phenyl-2-decanoylamino-3-morpholino-1-propanol (PDMP) and increased by the inhibition of β-glucosidase with conduritol B epoxide. See Shayman, J. A. et al., *J. Biol. Chem.* 266(34):22968–22974 (1991). Decreased glycolipid formation was associated with a pronounced impairment of cell growth, whereas increased GlcCer formation induced cell proliferation. Decreasing glycolipid formation was also associated with a pronounced increase in hormone-stimulated inositol triphosphate (InsP3) formation, wherein the increased GlcCer formation had the opposite effect. Shayman, J. A. et al., *J. Biol. Chem.* 265:12135–12138 (1990); Mahdiyoun, S. et al., *Arch. Biochem. Biophys.* 292:506–511 (1992). These results implicated cellular GlcCer, or a metabolically close product of GlcCer metabolism, as a regulator of MDCK cell growth.

While glycosphingolipids have been generally studied as elements in cellular proliferation and regulation of hormonal signaling, and also implicated in tumor growth (see U.S. Pat. No. 5,041,441 to Radin et al.), they have not been previously linked to diabetic nephropathy. In fact, the potential pathogenic role of glycosphingolipids in the treatment of diabetic nephropathy has not heretofore been explored.

It would be desirable to develop an effective method for preventing diabetic nephropathy. It would also be desirable to develop an effective method for treating diabetic renal impairment. It would further be desirable to develop an effective method of reversing diabetic renal impairment.

SUMMARY OF THE INVENTION

The present invention is a novel method for the treatment of renal hypertrophy and hyperplasia associated with diabetic nephropathy. The claimed method provides a method for preventing or ameliorating the increased growth in diabetic patient kidneys. The method of the present invention generally comprises the administration to the diabetic patient of compounds which inhibit glycosphingolipid synthesis, more particularly, inhibitors of glucosylceramide (GlcCer) synthase and 3-ketodihydrosphingosine synthase.

Inhibitors useful in the present invention include those of the general formula set forth below (hereinafter "Formula I") which inhibit GlcCer synthase:

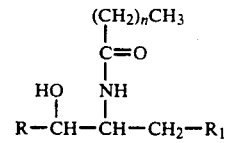

where R is an aromatic ring, a cyclohexane, or an aliphatic group having 10 to 15 carbon atoms; $R_1$ is an amine group; and n is an integer of from about 4 to about 18. More preferably, R is phenyl; $R_1$ is a morpholino group; and n is an integer from about 4 to about 18, and the inhibitor is 1-phenyl-2-acylamino-3-morpholino-1-propanol.

Inhibitors of 3-ketodihydrosphingosine synthase include e.g. L-cycloserine, and β-chloroalanine. Holleran, W. M. et al., *J. Clin. Invest.* 88:1338 (1991); Medlock et al., *Biochem.* 27:7079 (1988).

The above compounds, their functional homologues and pharmaceutically useful salts thereof, are useful in preventing the early changes in renal function associated with diabetes mellitus and thereby prevent long term renal impairment in the diabetic patient. By "functional homolog" is generally meant that the homologous compound retains glycosphingolipid inhibitory characteristics. The compounds are also useful in treating renal hypertrophy and hyperplasia which accompanies early diabetic nephropathy and, thus, are useful in preventing long term renal injury. The compounds of the present invention prevent or reverse renal hypertrophy associated with diabetic nephropathy.

DETAILED DESCRIPTION OF THE PREFERRED EMBODIMENTS

The compounds of Formula I, the individual optical isomers thereof, pharmaceutically useful salts thereof and hydrated as well as non-hydrated forms thereof are known in the art and can be readily prepared by procedures described in the art. See, e.g., Abe, A. et al, *J. Biochem.* 111:191-196 (1992); and Inokuchi, J. et al., *J. Lipid Res.* 28:565-571 (1987). L-cycloserine is available through Sigma Chemical Co., (St. Louis, Mo.). See Shukla, G. S. et al., *Biochem. Biophys. Acta* 1083:101 (1991). In general, n in the compounds of Formula I comprises an integer of from about 4 to about 18. In a more preferred embodiment, n is 4, 6, 8, 10, 12 or 14. In a most preferred embodiment, n is the integer 8 or 12. Also, the D-enantiomer of the compounds of Formula I is preferred in practicing the present invention.

The method of the present invention finds use in any patient diagnosed as having diabetes mellitus. The compounds of Formula I would be administered to the diabetic patient preferably upon being diagnosed as having diabetes in order to prevent or ameliorate the renal hypertrophy associated with diabetic nephropathy. The compounds of Formula I may also reverse renal hypertrophy or ameliorate renal damage in those patients who have experienced diabetes mellitus for longer periods of time.

In practicing the method of the present invention, the amount of compound of Formula I to be administered will vary with the patient being treated and will be monitored on a patient by patient basis by the physician. Generally, the smallest effective dose will be administered for each patient, and it is presently anticipated that from about 5 milligrams per kilogram (mg/kg) to about 200 mg/kg of body weight of the patient, will be effective. The compounds of Formula I can be formulated for oral or parenteral administration by procedures well established in the pharmaceutical arts using a variety of fillers and excipients to improve the quality of the dosage form. In addition, because metabolism of PDMP is cytochrome P450 dependent, carrying out the method of the present invention, it may also be desirable to co-administer an inhibitor of cytochrome P450, such as cimetidine, with the compounds of Formula I.

Inhibitors of 3-ketodihydrosphingosine synthase, such as L-cycloserine and $\beta$-chloroalanine and pharmaceutically useful salts thereof can also be employed in the practice of the present invention. With respect to L-cycloserine, it is presently anticipated that about 30 to about 50 mg/kg body weight of the patient will be effective.

In carrying out the Specific Examples described below, the materials and methods utilized herein are described in greater detail in the Materials and Procedures section below.

MATERIALS AND PROCEDURES

Materials

GlcCer was isolated from the spleen of a patient with Gaucher disease. Radin, N. S., *J. Lipid Res.* 17:290-293 (1976). Galactosylceramide from bovine brain was obtained from Serdary (Port Huron, Mich.). Ganglioside standards were obtained from Matreya, Inc. (Pleasant Gap, Pa.). NBD-GlcCer, streptozotocin, UDP-Glc (from yeast), UDP-Glc dehydrogenase (from bovine liver), and Na taurocholate were obtained from Sigma Chemical Co. (St. Louis, Mo.). Ultralente lletin I insulin was obtained from Eli Lilly and Co. (Indianapolis, Ind.). Sprague-Dawley rats were obtained from Harlan Industries (Indianapolis, Ind.).

Induction of Diabetes

Because there is gender specific expression of renal GSLs, only male rats were used. Shukla, A. et al., *am. J. Physiol.* 262: F24-F29 (1992). Male rats were fed a standard pellet laboratory chow and were provided with water ad libitum. Diabetes was induced by the administration of streptozotocin (80 mg/kg i.p.) dissolved in 10 mM Na citrate, pH 5.5. Controls were injected with buffer alone. Animals were provided with immediate access to food. Blood was obtained from the tail vein and blood glucose levels were determined with a Beckman glucose analyzer 48 h following the injection and at the time of organ resection. Animals with blood glucose levels greater than 35 mM were hypercatabolic and did not reliably exhibit renal hypertrophy. Therefore only animals with blood glucose concentrations between 13.5 and 32 mM were utilized. At the end of the experimental period, the animals were weighted, anesthetized with ether, and their kidneys removed and weighed. For UDP-Glc measurements, the kidneys were frozen in liquid nitrogen immediately following removal.

Glycolipid Analysis

To analyze the glycolipid content of tissues, kidneys were homogenized in 10 vols of chloroform:methanol (1:1) with a Polytron (Brinkmann Instruments), and the homogenates were filtered through a sintered glass funnel. The pellet was extracted twice with 10 ml of chloroform:methanol (1:2), and the pooled extracts were evaporated to dryness and radissolved in chloroform:methanol:water (30:60:8). The lipid extracts were analyzed as previously described in Shayman, J. A. et al., *J. Biol. Chem.* 266:2298 (1991).

TLC plates were sprayed with a cupric sulfate charring reagent (Touchstone, J. C. et al, *Clin. Chem.* 29:1951-1954 (1983)) made by a recently described modification. Shukla, G. S. et al., *Biochem. Biophys. Akia* 1083:101-108 (1991). Lipids were quantitated by densitometry by comparison to known amounts of authentic standards. Only the nonhydroxy GlcCer bands were measured.

UDP-Glc Determination

UDP-Glc was assayed enzymatically by the method described in Keppler, D. et al., *Anal. Biochem.* 38:105-114 (1970). In brief, frozen kidneys were weighed and homogenized in 5 vols of 0.6N perchloric acid. The homogenate was centrifuged at 1000 g and KHCO$_3$ was added to the supernatant to achieve a pH of 8.5. The KClO$_4$ was removed by centrifugation. A portion of the supernatant (0.2 to 0.4 ml) was added to 0.5 ml of glycine-KOH (0.5M, pH 8.7) containing 3 mM NAD+ and 6 mM sodium EDTA. Water was added to yield a final volume of 1 ml. UDP-Glc dehydrogenase (10 μl, 0.09 U) was added and the UV absorbance was measured immediately and 10 min later.

Enzyme Assays

Prior to performing enzyme assays, the kidneys were stored at −70° C. and homogenized in 9 vols of water. Aliquots of each homogenate were assayed in duplicate. Glucosylceramide β-glucosidase (EC 3.2.1.45) was assayed with the fluorogenic substrate, NBD-GlcCer, with 0.1-0.2 mg of tissue in a total volume of 0.2 ml. Dinur, T. et al., *Anal. Biochem.* 38:105-114 (1970). GlcCer from Gaucher spleen, Triton X-100, Na taurocholate and phosphate-citrate buffer (pH 5.0) were employed. Ceramide:UDP-Glc glucosyltransferase (EC 2.4.1.80) was assayed with an improved method utilizing NAD to protect the nucleotide sugar against pyrophosphatase. Shukla, G. S. et al., *Arch. Biochem. Biophys.* 283:372-378 (1990).

PDMP Treatment

The GlcCer synthase inhibitor PDMP was administered as the DL-hydrochloride to both diabetic and control animals 14 days following the induction of diabetes with streptozotocin (see Table IV results). Previous studies have demonstrated that the circulating plasma levels of PDMP are prolonged in the presence of the cytochrome P450 inhibitor, piperonyl butoxide. See Shukla, A. et al., *J. Lipid. Res.* 32:713-722 (1991). The piperonyl butoxide was prepared by dissolution in corn oil at a concentration of 150 mg/ml oil. The butoxide solution was administered intraperitoneally prior to injection of PDMP. On the first day of treatment this was given 4 h before PDMP treatment; on days 2 to 4 of treatment it was administered just prior to the PDMP injection. PDMP was prepared as an emulsion with the detergent Myrj 52 in normal saline, buffered with sodium acetate. The final concentrations of PDMP, Myrj 52 and sodium acetate in mg/ml were 6, 12, and 8 respectively. The PDMP was given intraperitoneally as a dose of 100 mg/kg body weight.

Glomerular Morphometry

Glomerular volumes were measured on paraffin sections of kidney fixed in formalin and stained with periodic acid Schiff reagent. The measurements required the determination of the mean glomerular random cross sectional area (A(G)). Glomerular areas were measured using a Javelin Chromachip camera (Javelin Electronics, Torrance, Calif.) attached to an Olympus BH-2 microscope interfaced with a Macintosh II computer containing an Image Capture 2 frame grabber (Scion Corp., Walkerville, Md.) and image 1.38B14 software (NIH Public Software, Bethesda, Md.). Glomerular volumes were derived by the method described in Weibel "Stereological Methods. Practical Methods for Biological Morphometry," (academic Press, London) p. 44-45 (1979) as applied by Hirose, K. et al., *Kidney Int.* 21:689-695 (1982).

The following Specific Examples further describe the present invention.

SPECIFIC EXAMPLE 1

Preliminary experimentation confirmed the presence of glycosphingolipid (GSL) changes in both diabetic rat kidney and human mesangial cells cultured under hyperglycemic conditions. Table I displays the levels of sphingolipids in male rats with streptozotocin-induced diabetes. The data are expressed as μg/g wet weight for GlcCer, N-acetylneuraminyl galactosylglucosylceramide (ganglioside GM3), and ceramide and mg/g wet weight for sphingomyelin. The values are represented as the mean ± standard deviation (S.D.). As shown in Table I, both kinds of cerebrosides, GlcCer and galactosylceramide, were significantly elevated. In addition, ganglioside GM3 levels were significantly higher in the diabetic animals. The precursor sphingolipid, ceramide, was not significantly different between the two groups of animals.

Nucleotide sugars were also assayed. Both UDP-Glc and UDP-Gal were high in diabetic kidneys. (UDP-Glc (nmol/g wet weight kidney): 35±2.8 versus 60.8±9.3; UDP-Gal 25±1.8 versus 30.0±1.8 in control versus diabetic respectively (p<0.05 by paired t analysis). This confirms the previous reports of Spiro, M. J. *Diabetologia* 26:70-75 (1984) and Cortes, P. et al., *Kidney. Int.* 21:676-682 (1982). The elevation of galactosylceramide and UDP-Gal is not surprising given the presence of an epimerase which interconverts the two nucleotides.

Preliminary experimentation was also conducted assaying the GlcCer synthase of control and diabetic kidneys. The activity of the synthase varied with tissue concentration due to the presence of a pyrophosphatase which degrades UDP-Glc. However, when normalized for tissue weight, no difference in synthase activity was noted between the two groups. These data are consistent with the interpretation that the increased sphingolipid levels are primarily a consequence of increased substrate availability.

TABLE I

| Sphinogolipid levels of rat kidneys. | | | |
|---|---|---|---|
| | Control | Diabetic | Percent Change |
| GlcCer | 26.1 ± 5.1 | 32.5 ± 5.9* | +25 |
| ganglioside GM3 | 46.4 ± 9.8 | 63.7 ± 6.4* | +37 |
| ceramide | 177 ± 18.5 | 159 ± 15.0 | −10 |
| sphinogomyelin | 2.54 ± 0.39 | 2.23 ± 0.38 | −12 |

*denotes p<0.05 by paired t test, n = 10

SPECIFIC EXAMPLE 2

Three groups of male rats, having 6 rats per group, weighing an average of 113 g (range 105 to 124 g) were made diabetic with streptozotocin. After 24 h, one group of rats was treated with daily injections of Ultralente Iletin insulin at an initial dose of 0.03 U/g body weight. Daily blood glucose determinations were made and the insulin dose adjusted for each rat to approach euglycemia. As shown in Table II below, wherein the data are expressed as the mean ± S.D. for six animals per group exhibiting a mean blood glucose of 15.9±0.7 mM during days 2 through 12, initially the rats responded poorly to the insulin. However, their glucose levels normalized toward the end of the experimental period.

In spite of an increased caloric intake, the untreated diabetic rats weighed significantly less (27%) than the control rats by the end of the experimental period, as reflected by the body weight set forth in Table II. The insulin-treated rats, however, maintained the same body weight as the control rats. The kidney weights of the untreated diabetic rats were 20% larger than those of the control and insulin-treated groups. When normalized for body weight the increase was even more pronounced (63%).

TABLE II

Characteristics of control, diabetic and insulin-treated rats.

| | Body Weight (g) | Kidney Weight (g) | Kidney Weight/ Body Weight (g/100 g) | Blood Glucose (mM) |
|---|---|---|---|---|
| Control | 280 ± 7.2 | 2.73 ± 0.13 | 0.98 | 9.1 ± 0.13 |
| Diabetic | 204 ± 8.2 | 3.28 ± 0.16 | 1.60 | 21.1 ± 1.36 (day 2) 22.6 ± 1.21 (day 15) |
| Insulin-treated | 284 ± 4.0 | 2.78 ± 0.11 | 0.96 | 26.3 ± 3.12 (day 2) 6.6 ± 1.22 (day 15) |

Glycosphingolipid and UDP-Glc measurements were performed on the kidneys and the results are set forth in Table III below. In Table III, UDP-Glc levels are expressed as nmol/g wet weight of kidney. The data for GlcCer and ganglioside GM3 are expressed as $\mu g/g$ wet weight. The GlcCer data represent densitometric measurements from the fastest moving cerebroside spot (representing cerebrosides not containing phytosphingosine or 2-hydroxy fatty acids), although all spots migrating as cerebrosides increased visibly in the diabetic kidneys.

As shown in Table III, significant increases in both GlcCer (45%) and ganglioside GM3 concentrations (68%) were observed in the diabetic animals. Insulin treated rats had renal GlcCer levels that were slightly higher than control but significantly lower than the diabetic group. The increase in ganglioside GM3 observed in the diabetic rats also was corrected by insulin treatment. UDP-Glc levels were significantly higher (59%) in the untreated diabetic animals and were partially, but significantly normalized by the insulin treatment. Water comprises approximately 76% of the wet weight of the kidneys. Weinberg, J. M. et al., *Exp. Mol. Pathol.* 39:43–60 (1983). Assuming that one-third of the water was in extracellular compartments and that all of the UDP-Glc is intracellular, the estimated intracellular tissue concentrations of UDP-Glc would be 149, 237, and 199 $\mu M$ in control, diabetic and insulin-treated kidneys respectively.

TABLE III

| Glycosphinogolipid and UDP-Glc levels. | | | |
|---|---|---|---|
| | Control | Diabetic | Insulin-Treated |
| GlcCer | 29.4 ± 0.91 | 37.8 ± 1.42* | 33.5 ± 1.21 |
| ganglioside GM3 | 43.9 ± 3.13 | 65.4 ± 6.46* | 44.3 ± 12.5 |
| UDP-Glc | 78.4 ± 4.1 | 125 ± 7.3* | 105 ± 8.14 |

*denotes p<0.05 by analysis of variance and the Scheffe F test. The data are expressed as the mean ± S.D. (n = 6).

In order to ascertain the basis for the increase in cerebroside levels in the untreated diabetic animals, GlcCer $\beta$-glucosidase and GlcCer synthase activities were measured, and the results are set forth in Table IV below. In Table IV, glucosylceramide $\beta$-glucosidase activity is expressed as nmol/mg tissue/h ± S.E.; GlcCer synthase activity is expressed as pmol/mg tissue/h ± S.E. $\beta$-glucosidase and GlcCer synthase assays utilized 0.2 mg and 2.0 mg of kidney respectively. Values were not significantly different by paired t test, n = 6.

As shown in Table IV, neither $\beta$-glucosidase nor GlcCer synthase activity was different when compared to the control group. These data are consistent with the interpretation that increased cerebroside levels were likely due to an increase in the levels of UDP-Glc, a precursor for glucosphingolipid synthesis. To further support this interpretation, the apparent $K_m$ for UDP-Glc of the rat renal GlcCer synthase was measured. The apparent $K_m$ was 250 $\mu M$ in both normal and diabetic kidney. This concentration is of the order of or significantly greater than that calculated based on the observed contents of UDP-Glc. Since glucosylceramide synthase is topologically localized to the cytosolic side of the Golgi membrane, the cytosolic distribution of renal UDP-Glc was measured. Coste, H. et al., *Biochem. Biophys. Acta* 858:6–12 (1986); and Futerman, A. H. et al., *Am. J. Physiol.* 260:F291–F302 (1991). Kidneys homogenized immediately following resection were centrifuged at 263,000× g for 10 min at 4° C. Under these conditions, greater than 94% of the UDP-Glc remained in the cytosolic fraction and less than 6% remained in the unwashed particulate fraction.

TABLE IV

| GlcCer metabolyzing enzyme activities. | | |
|---|---|---|
| | Control | Diabetic |
| $\beta$-glucosidase | 211 ± 13.5 | 200 ± 13.5 |
| GlcCer synthase | 58 ± 1.6 | 59 ± 1.3 |

The data set forth in Tables III and IV, showing an accumulation of GlcCer and ganglioside GM3 in the diabetic rat kidneys (Table III) and no substantial change in levels of $\beta$-glucosidase or GlcCer synthase (Table IV), indicate that the increased levels of glucolipids were due to increased levels of the substrate UPD-Glc. These findings are consistent with the findings of Cortes, P. et al., *Kidney Int.* 21:676–682 (1982) and Spiro, M. J. *Diabetologia* 26:70–75 (1984), who have reported an increase of uridine diphosphohexoses in rat kidneys following experimentally induced diabetes.

SPECIFIC EXAMPLE 3

To determine whether the increase in glucolipid formation in diabetes was functionally important, the following experiment was performed. One group of animals was made diabetic with streptozotocin, and the other group received vehicle alone. After two weeks, the control and diabetic groups were divided according to the weights of the rats. Half of the non-diabetic and half of the diabetic animals received DL-threo-PDMP, which is the racemic mixture of the compound of the Formula I where n is 8. The control non-diabetic and diabetic groups were pair fed and received vehicle alone. After 4 days of treatment the animals were weighed and sacrificed. The characteristics of these animals are shown in Table V below. In Table V, the data are expressed as the mean ± S.D. All animals received the cytochrome P450 inhibitor piperonyl butoxide (600 mg/kg) intraperitoneally. Treated control and diabetic animals received DL-threo-PDMP.

As shown in Table V, the body weights of the treated and untreated non-diabetic animals were not significantly different. The weights of the diabetic rats were significantly lower than the nondiabetic groups but were no different between PDMP-treated and untreated animals. Kidney weights, however, did differ significantly. The diabetic animals displayed kidney weights that were significantly greater than the control animals. The kidney weights of the diabetic animals treated with PDMP, however, were significantly lower than those of the untreated diabetic animals in spite of the fact that these animals were significantly hyperglycemic. The serum creatinines of the diabetic animals were lower than those of the control groups, reflective of the lower body weights. The blood urea nitrogen (BUN) levels were higher among the diabetic animals, consistent with the significant level of hyperglycemia.

TABLE V

Characteristics of control and diabetic rats treated with PDMP.

| GROUP | n | Body Weight (g) | Kidney Weight (g) | Glucose (mM) | BUN (mg/dl) | Creatinine |
|---|---|---|---|---|---|---|
| Control | 12 | 241 ± 16 | 2.30 ± 0.17 | 10.1 ± 0.83 | 15 ± 2.4 | 0.28 ± 0.07 |
| Control + PDMP | 11 | 238 ± 21 | 2.25 ± 0.27 | 9.38 ± 0.89 | 13 ± 3.2 | 0.31 ± 0.09 |
| Diabetic | 7 | 203 ± 23 | 2.62 ± 0.29* | 25.9 ± 3.22 | 24 ± 5.7 | 0.23 ± 0.05 |
| Diabetic + PDMP | 7 | 200 ± 11 | 2.32 ± 0.19 | 25.9 ± 4.33 | 28 ± 6.4 | 0.23 ± 0.05 |

*denotes $p<0.001$ by one way analysis of variance using the Scheffe test.

Renal histology was performed to ascertain if the drug treatment induced significant toxicity. Periodic acid Schiff stained sections of kidney revealed no evidence of acute tubular necrosis, acute or chronic inflammation, or glomerular pathology. There was an apparent increase in the size of the glomeruli of the diabetic animals. This increase, however, was not obvious in the inhibitor treated diabetic animals.

Five kidneys from each group of animals were studied by morphometric analysis. Glomerular areas were determined on randomly sectioned kidney from each group. Every available glomerulus from each section was measured. The mean glomerular volume of diabetic kidneys was 28% greater than that of the control kidneys. PDMP treatment of the non-diabetic rats had no effect on glomerular size. However, the glomerular volumes of diabetic animals treated with PDMP were not significantly different from those of the control groups.

The increase in glucosphingolipid content in the kidney of streptozotocin induced diabetic rats shown by the data contained herein indicate the importance of a quantitatively minor route for glucose utilization in hyperglycemic states. The data set forth in Table V show that administration of a representative compound of Formula I reverses the early hypertrophy of insulin deficient diabetes mellitus and provides a new pharmacological approach to the treatment of diabetic complications.

SPECIFIC EXAMPLE 4

To evaluate the efficacy of GlcCer synthase inhibitor homologues and the 3-ketodihydrosphingosine synthase inhibitor in revering diabetic hypertrophy, the following experiments are performed.

Male rats weighing approximately 100 g are made diabetic with 75 mg/kg of streptozotocin. At this dose approximately 60% of the animals attain long term hyperglycemia in the range of about 250 mg/dl to about 500 mg/dl without insulin administration. Animals are monitored with blood glucose determinations every 3 days prior to exposure to sphingolipid inhibitors. Metabolism of PDMP is cytochrome P450 dependent. Exposure of animals to the mixed function oxidase inhibitor PB prolongs the half life of PDMP from 1 to 4 h. (PB alone has no effect on renal growth or function.) Animals receiving the GlcCer synthase inhibitors are injected i.p. with PB (600 mg/kg in corn oil) 4 h prior to receiving the lipid inhibitors. PMMP or PMMP is injected following dissolution in Myrj 52 detergent (12 mg/ml). Control groups receive piperonyl butoxide and Myrj alone. These animals are pair fed with their comparable control groups by weighing the food ingested from the previous 24 h. In previous experiments, pair fed animals maintained weights that were within 2% of their experimental groups.

In the first series of experiments the ability of PDMP to reverse diabetic hypertrophy is assessed. Diabetes is induced and the animals followed for 4, 8 and 16 weeks.

At the end of the experimental period, control and diabetic groups are treated for four days with PB and DL-PDMP or PB and vehicle alone. One day prior to inhibitor treatment and on the last day of treatment the animals are placed in metabolic cages for collection of urine for protein determination. The kidneys are removed, weighed, and either fixed for histology or rapidly frozen for lipid analysis. The kidneys are analyzed for UDP-hexose levels, neutral and acidic GSL content, sphingol levels and ceramide content.

In the second series of experiments, diabetic and control animals are followed for 4 weeks. Animals are then treated with L-cycloserine (40 mg/kg), both agent and vehicle or vehicle alone. Control animals are pair fed. Proteinuria is assessed. Lipid and UDP-hexose levels are assayed as detailed above.

In the third series of studies the effects of the myristoylated homologue, PMMP, is compared to PDMP. Animals are made diabetic and followed for 4 weeks. Treatment groups receive different doses of GlcCer synthase inhibitor ranging from about 20 mg/kg/d to about 100 mg/kg/d. Animals are closely followed for toxicity, which has been found acceptable in other studies. Radin, N. et al., *Biochem. Pharmacol.* 37: 2879–2886 (1988).

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the specification and following claims.

All publications and patents cited herein are incorporated by reference.

We claim:

1. A method for treating renal hypertrophy associated with diabetic nephropathy in mammals comprising the step of administering to a mammal in need of such treatment a therapeutically effective amount of an inhibitor of glycosphingolipid synthesis.

2. The method of claim 1, wherein the inhibitor is an inhibitor of glucosylceramide synthase.

3. The method of claim 1, wherein the inhibitor is an inhibitor of 3-ketodihydrosphingosine synthase.

4. The method of claim 2, further comprising the step of administering a therapeutically effective amount of an inhibitor of 3-ketosphingosine synthase.

5. The method of claim 2, wherein the inhibitor is a compound selected from the group consisting of compounds of the Formula I:

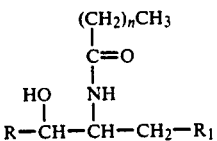

where R is an aromatic ring, a cyclohexane, or an aliphatic group having 10 to 15 carbon atoms; $R_1$ is an amine group; and n is an integer from about 4 to about 18; and functional homologues, isomers and pharmaceutically useful salts thereof.

6. The method of claim 3, wherein the inhibitor is selected from the group of compounds consisting of L-cycloserine, β-chloroalanine and functional homologues, isomers and pharmaceutically useful salts thereof.

7. The method of claim 6, wherein the group consists of L-cycloserine, functional homologues, isomers and pharmaceutically useful salts thereof.

8. A method for treating kidney hypertrophy associated with diabetic nephropathy in a patient comprising the step of administering to the patient a therapeutically effective amount of an inhibitor of glucosylceramide synthase comprising a compound selected from the group consisting of compounds of the Formula I:

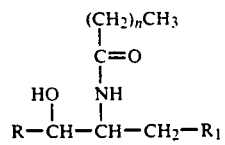

where R is an aromatic ring, a cyclohexane, or an aliphatic group having 10 to 15 carbon atoms; $R_1$ is an amine group; and n is an integer of from 4 to 18; and functional homologues, isomers and pharmaceutically useful salts thereof.

9. The method of claim 8, wherein n is an integer of from 4 to 14.

10. The method of claim 8, further comprising the step of administering an inhibitor of 3-ketosphingosine synthase selected from the group consisting of L-cycloserine, β-chloroalanine and functional homologues, isomers and pharmaceutically useful salts thereof.

11. The method of claim 9, wherein n is the integer 4, 6, 8, 10, 12 or 14.

12. The method of claim 11, wherein n is the integer 8 or 12.

13. The method of claim 12, wherein n is the integer 8.

14. A method for treating diabetic nephropathy in a patient comprising the step of administering to the patient a therapeutically effective amount of a 3-ketodihydrosphingosine synthase inhibitor.

15. The method of claim 14, further comprising the step of administering a therapeutically effective amount of an inhibitor of glucosylceramide synthase.

16. The method of claim 14, wherein the inhibitor is selected from the group consisting of L-cycloserine, β-chloroalanine and functional homologues, isomers and pharmaceutically useful salts thereof.

* * * * *

UNITED STATES PATENT AND TRADEMARK OFFICE
CERTIFICATE OF CORRECTION

PATENT NO. : 5,302,609
DATED : April 12, 1994
INVENTOR(S) : James A. Shayman and Norman S. Radin It is certified that error appears in the above-indentified patent and that said Letters Patent is hereby corrected as shown below:

On the Title Page, on page 2 of "Other Publications", line 11, "Development" should be --"Development--.

On the Title Page, on page 2 of "Other Publications", line 12, after "Rat" insert --"--.

Column 1, line 40, "1991)" should be --(1991)--.

Column 1, lines 44-45, "(UPD-hexose)" should be --UDP-hexose--.

Column 2, line 2, "endogneous" should be --endogenous--.

Column 2, line 13, "triphosphate" should be --trisphosphate--.

Column 4, line 16, "Spraque" should be --Sprague--.

Column 4, line 21, "am." should be --Am.--.

Column 4, line 22, "262: F24-F29" should be --262:F24-F29--.

Column 4, line 36, "weighted" should be --weighed--.

Column 4, line 50, "radissolved" should be --redissolved--.

UNITED STATES PATENT AND TRADEMARK OFFICE
CERTIFICATE OF CORRECTION

PATENT NO. : 5,302,609
DATED : April 12, 1994
INVENTOR(S) : James A. Shayman and Norman S. Radin It is certified that error appears in the above-indentified patent and that said Letters Patent is hereby corrected as shown below:

Column 5, line 64, "(academic" should be --(Academic--.

Column 9, line 54, "revering" should be --reversing--.

Col. 10, line 1, "PMMP" (first occurrance) should be --PDMP--.

Signed and Sealed this

Eighteenth Day of October, 1994

Attest:

BRUCE LEHMAN

*Attesting Officer*  *Commissioner of Patents and Trademarks*